United States Patent [19]

Houben et al.

[11] 4,003,242
[45] Jan. 18, 1977

[54] DEVICE FOR DETERMINING THE MIXING RATIO OF BINARY GASES

[75] Inventors: Heinz Houben, Monchengladbach; Manfred Pabst, Weiden near Cologne, both of Germany

[73] Assignee: A. Monforts, Monchengladbach, Germany

[22] Filed: July 14, 1975

[21] Appl. No.: 595,494

[30] Foreign Application Priority Data

July 13, 1974 Germany ............................ 2433764

[52] U.S. Cl. ................................. 73/24; 137/804
[51] Int. Cl.² ..................... G01N 29/02; F01C 1/04
[58] Field of Search ............ 73/23, 23.1, 32 R, 24; 137/804, 828, 835, 836, 841

[56] References Cited
UNITED STATES PATENTS

| 3,299,255 | 1/1967 | Bauer | 137/804 |
|---|---|---|---|
| 3,504,691 | 4/1970 | Campagnuolo et al. | 137/835 |
| 3,554,004 | 1/1971 | Rauch et al. | 73/23 |
| 3,616,809 | 11/1971 | Laakaniemi et al. | 137/804 |
| 3,665,947 | 5/1972 | Mayer | 137/804 |
| 3,915,645 | 10/1975 | Funke et al. | 73/23.1 |

OTHER PUBLICATIONS

Akmenkalns et al., IBM Technical Disclosure Bulletin, "Pneumatic to Electric Transducers," vol. 5, No. Dec. 1962, pp. 14–15.
Noble et al., Analytical Chemistry, "Performance and Characteristics of an Ultrasonic Gas Chrom. Effluent Detector," vol. 36, pp. 1421–1427, July 1964.

Primary Examiner—Richard C. Queisser
Assistant Examiner—Stephen A. Kreitman
Attorney, Agent, or Firm—Herbert L. Lerner

[57] ABSTRACT

Device for determining the mixing ratio of binary gases in a mixture thereof by measuring the velocity of sound in the gas mixture, the value of the velocity of sound in the gas mixture determined by the oscillating frequency of a fluidic oscillator, the absolute temperature ($T_r$) of the gas mixture in the feedback means of the oscillator, a correction factor proportional to the difference between the absolute temperature ($T_r$) and the predetermined temperature ($T_o$).

9 Claims, 10 Drawing Figures

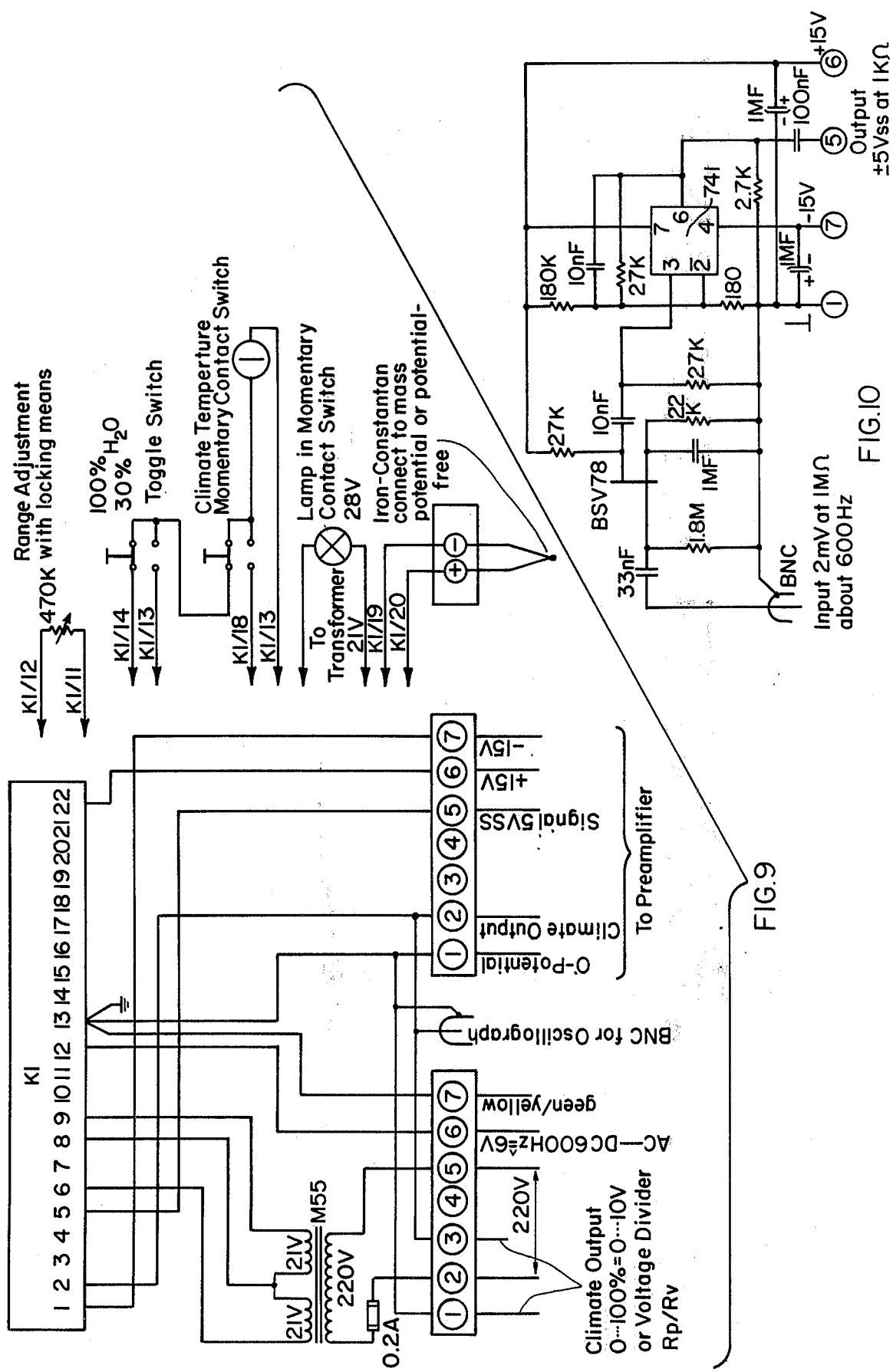

DEVICE FOR DETERMINING THE MIXING RATIO OF BINARY GASES

The invention relates to a device for determining the mixing ratio of binary gases by the determination of the sound velocity of the gas mixture by means of the oscillator frequency of a fluidic oscillator (wall attachment fluid element). Such a device is preferably a component of a control system for adjusting the mixing ratio of two or more gases in a processing chamber. Such control systems or installations are employed amongst others in different processes for textile modification or improvement, for example, to adjust specific mixtures of air and water vapor in treatment or processing machines. Circulating air dryers are thus generally operated with a water-vapor content of approximately 20% in the circulating air, since the drying efficiency and drying energy is optimum at this very value. Other processes which require, for example, the exclusion of air or oxygen, are carried out with as close as possible to a 100% water-vapor atmosphere. Even further processes are supposed to take place in a treatment or processing atmosphere having a given percentage of solvents, such as 90 to 95% perchlorethylene, for example.

Since conventional measurement and control devices for registering the absolute or relative humidity, such as hair hygrometers, lithium-chloride moisture-sensors, psychrometers or moisture sensors with a synthetic foil (cf. "Control of exhaust air moisture for dryers of textile webs", Textil-Praxis (Textile Practice) Stuttgart S. 1960, Book 11, pages 1151 to 1157 and Book 12, pages 1271 to 1279), are suitable only for measurement or control processes up to temperatures of about 100° C, it has been suggested that the velocity of sound of a gas mixture in the processing chamber be employed as a measure of the water-vapor concentration i.e. as a measure of the mixing ratio.

The velocity of sound in a gas, as is generally known, depends upon the respective type thereof or the composition thereof. Assuming that sound propagation is considered to be substantially an adiabatic process, and the air, hereinafter considered to be a gas, as well as superheated steam at normal pressure and temperatures of 0° to 300° C are considered substantially as ideal gases, then the velocities of sound in gases at the same temperature are dependent upon the different respective mole-weights and polytropic exponents. The polytropic exponent is the quotient of the specific heat at constant pressure and the specific heat at constant volume. In the process according to the invention, the gases of the mixture to be determined are, of course, at the same temperature. The respective sound velocities $a_1$ and $a_2$ therefore depend upon the following relationship of the mole-weights $M_1$ and $M_2$ and the polytropic exponents $K_1$ and $K_2$:

$$\frac{a_1}{a_2} = \sqrt{\frac{M_2 \cdot K_1}{M_1 \cdot K_2}}$$

As shown hereinafter in the plot diagram of FIG. 1, for different temperatures ($T_1 = 100°$ C $= 373°$ K, $T_2 = 150°$ C $= 423°$ K and $T_3 = 200°$ C $= 473°$ K), the velocity of sound a in m/sec. of an air-water vapor mixture is a function of the water-vapor concentration $x$ in this mixture. For example, it can be concluded from FIG. 1 that the difference in the velocity of sound in steam with respect to the velocity of sound in air is about 23%. For gases which differ more sharply in molecular weight, such as most organic solvents in air, for example, such differences become considerably greater. Thus, the ratio of the velocity of sound in air to that in perchlorethylene, for example, is 2.68 : 1. With mixtures of two gases, as shown in FIG. 1, the velocity of sound, in accordance with the mixing ratio, lies between the indicated or given limits, thus, for example between 1 and 1.23 for air-water vapor or 1 and 2.68 for air-perchlorethylene.

Since a close connection or correlation accordingly exists between the mixing ratio and the velocity of sound in that mixture, the chamber climate of a machine is then determinable or controllable by measuring the sound velocity therein.

Attempts have been made, heretofore, to employ fluidic oscillators (wall attachment fluid elements) for measuring the velocity of sound in a mixture. The frequency of fluidic oscillators, as is generally known, is dependent upon the temperature (H. J. Tafel "Analog or digital signalling technique in fluidics?", a paper presented at the technical conference on oil hydraulics and pneumatics, Hannover Fair 1971, Conference Report Volume, especially pages 126 to 131). This dependence results from the different densities of the gases at different temperatures. The frequency of these oscillators is thereby dependent upon the velocity of sound in the gas (besides the geometry of the oscillators proper). From the frequency of oscillation of a fluidic oscillator the composition of the mixture, for example of an air/water vapor mixture, is determinable.

In the application of fluidic oscillators in accordance with the invention, it can be initially assumed that the individual components of the gas mixture that is to be measured are at the same temperature, but fluctuations of the temperature of the mixture itself cannot be excluded during the measuring. It is therefore an object of the invention to provide a device for determining the mixing ratio of binary gases wherein the effect of any temperature fluctuations is excluded from the measurement signal of the fluidic oscillator since, in the case of the invention of the instant application, the measurement signal should only depend upon the mixing ratio of the gas mixture that is to be measured. The elimination of temperature effects is particularly important since these effects influence the measurement signal of the fluidic oscillator not only by changing the velocity of sound in the gas mixture but also, since the feedbacks of the oscillator, especially in the feedback lines extending from the fluidic oscillator, experience a change in length during a change in temperature.

The frequency of a fluidic oscillator is also dependent, however, upon the applied differential pressure i.e. the pressure differential prevailing between the inlet and outlet of the fluidic oscillator. The pressure applied to the fluidic oscillator can vary due to fluctuations in the pump pressure, due to soiling of the apparatus or of a precoupled suction filter due to condensation of at least one component of the gas mixture to be measured, and the like, resulting in a erroneous measurement result. It is accordingly a further object of the invention to provide a device for determining the mixing ratio of binary gases wherein measurement errors due to pressure variations are avoided.

With the foregoing and other objects in view, there is provided, in accordance with the invention, a device for determining the mixing ratio of binary gases in a mixture thereof by measuring the velocity of sound in the gas mixture, that velocity being determined by the oscillating frequency of a fluidic oscillator comprising a fluidic oscillator tuned to a fundamental frequency ($f_o$) at a predetermined temperature ($T_o$) in air, the fluidic oscillator having inlet and outlet means and feedback means connecting the outlet means to the inlet means, means for detecting the oscillating frequency of the fluidic oscillator, which determines the velocity of sound in the gas mixture, and transmitting a signal corresponding thereto, measuring means for measuring absolute temperature ($T_g$) of the gas mixture at a location other than in the feedback means, correction means operatively connected to the means for measuring the absolute temperature ($T_g$) for correcting, by a correction factor proportional to the square root of the absolute temperature ($T_g$), the value of the velocity of sound in the gas mixture determined by the oscillating frequency of the fluidic oscillator and represented by the transmitted signal, measuring means for measuring absolute temperature ($T_r$) of the gas mixture in the feedback means, correction means operatively connected to the means for measuring the absolute temperature ($T_r$) for correcting, by a correction factor proportional to the difference between the absolute temperature ($T_r$) and the predetermined temperature ($T_o$), the value of the velocity of sound in the gas mixture determined by the oscillating frequency of the fluidic oscillator and represented by the transmitted signal, and pump means for pumping the gas mixture through the fluidic oscillator, the pump means being adjusted to a range of pressures wherein oscillating frequencies produced in the fluidic oscillator and serving to determine the respective velocity of sound in the gas mixture being pumped therethrough are independent of variations in the gas pressure.

In accordance with another feature of the invention, the correction means operatively connected to the means for measuring the absolute temperature ($T_g$) include means for multiplying the value of the velocity of sound in the gas mixture determined by the oscillating frequency of the fluidic oscillator and represented by the transmitted signal, by the square root of the quotient of the predetermined temperature ($T_o$) and the absolute temperature ($T_g$).

In accordance with a further feature of the invention, the correction means operatively connected to the means for measuring the absolute temperature ($T_r$) include means for adding the difference between the absolute temperature ($T_r$) and the predetermined temperature ($T_o$), multiplied by a constant factor, to the value of the velocity of sound in the gas mixture determined by the detected oscillating frequency of the fluidic oscillator and represented by the transmitted signal.

In accordance with an added feature of the invention, means are provided for shutting down the fluidic oscillator whenever the temperature of the gas mixture exceeds and falls below a predetermined range of temperatures.

In accordance with an additional feature of the invention, means are provided for measuring the pressure of the gas mixture in the fluidic oscillator and for shutting down the fluidic oscillator whenever the pressure of the gas mixture therein exceeds and falls below a predetermined range of pressures.

In accordance with yet another feature of the invention, the pump means is a suction pump.

In accordance with a further feature of the invention, means are interposed between the fluidic oscillator and the pump means for adding air to the gas mixture.

In accordance with a concomitant feature of the invention, means are provided for heating the air to the temperature of the gas mixture before adding the air to the gas mixture.

The absolute gas temperature ($T_g$) and the absolute temperature ($T_r$) of the feedback conduits can be equal and, in fact, generally are equal.

A result of the invention is that the value of the measurement signal received from the fluidic oscillator exclusively depends upon the mixing ratio of the gas mixture to be measured, and that all disruptive influences, such as changes in the length of the feedback channels or conduits due to temperature variations, the effect of the gas temperature, and the effect of soiling, for example, are eliminated. It has been found to be advantageous to tune or adjust the feedback lines of the fluidic oscillator, so that the fundamental frequency of the oscillator in air at 20° C and 65% relative humidity is approximately 600 Hz. Any error in measurement values due to elongation of the feedback paths when the feedback lines are heated, such error being linearly temperature-dependent, is compensated for by a simultaneous measurement of the temperature of the feedback lines, for example, electronically, insofar as the measurement of the gas temperature at a location other than in the feedback lines is not already adequate therefor. Moreover, any influence of the temperature of the gas mixture on the measurement signal of the fluidic oscillator, the oscillating frequency of which is proportional to the square root of the absolute temperature, is eliminated from the measurement signal by electronic additive or multiplicative compensation.

To eliminate the influence of fluctuations in the pressure applied to the fluidic oscillator, an element is selected which maintains the oscillating frequency virtually unchanged within a differential pressure range of 0.1 atmospheres. The pump supplying gas to the oscillator, according to the invention, is set or regulated to operate within this pressure range. The gas pressure of the differential pressure between inlet and outlet of the fluidic oscillator is therefore continuously measured advantageously and and the gas pump, based on that measurement value, is so controlled that the oscillator always operates within that predetermined differential pressure range. In this manner, any possible soiling of the filter at the inlet of the fluidic oscillator or at any other locations of the apparatus is also controlled, and, to the extent that the control of the gas pump permits, is even eliminated. Since an incorrect measurement signal would be obtained from the fluidic oscillator at a gas pressure outside of the predetermined pressure range, which is independent of frequency, it is advantageous for a signal to be given whenever the pressure has exceeded or has fallen below that pressure range, or for the system to be rendered inoperative, preferably automatically.

Furthermore, processes are known in the textile art, for example, wherein finishing materials (lubricants) or synthetic resins, which are present on the cloth, vaporize. It is particularly these materials which tend to clog the channels of fluidic oscillators. Since such processes, however, generally take place at temperatures which are above conventional drying temperatures in drying machines, the device according to the invention is automatically rendered inoperative especially as a result of automatic measurements, whenever the temperature has exceeded or fallen below a specific temperature threshold, so that no gaseous medium flows any longer through the channels of the fluidic oscillator.

Additionally, the invention of the instant application also applies to the adjustment and selection of the pump supplying the fluidic oscillator with gas. If, for example, the density of the gas mixture, that is to be measured, has been increased prior to the passage thereof through the fluidic oscillator with the air of the pressure pump, measurement error can then also occur due to changes in the gaseous state, especially during vaporization or steam formation, because of the danger of condensation. To avoid such error, a suction pump is provided, in accordance with the invention, to increase the differential pressure at the fluidic oscillator. This has the additional advantage that the pump can therefore be disposed outside the processing chamber.

If gas mixtures which contain a high water-vapor fraction are measured, then in accordance with the invention, in order to avoid condensate formation in the pump, it is advantageous to admix fresh air with the gas mixture sucked in by the pump behind the measurement element per se i.e. the fluidic oscillator. To avoid any deposition of condensate also during such admixture, the fresh air should advantageously be heated prior to such admixture to the temperature of the gas mixture that is to be measured.

Other features which are considered as characteristic for the invention are set forth in the appended claims.

Although the invention is illustrated and described herein as embodied in an apparatus for determining the mixing ratio of binary gases, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings in which:

FIG. 9 is a wiring diagram for the electronic system K1 of FIG. 8; and

FIG. 10 is a circuit diagram of the preamplifier of the fluidic oscillator.

Figure 1:
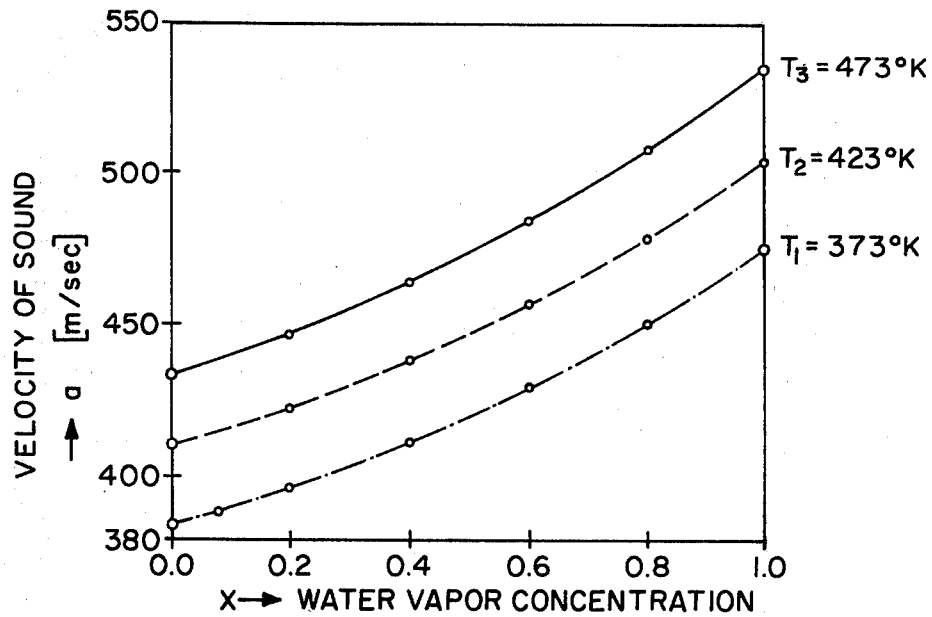
FIG. 1 is a plot diagram showing the velocity of sound in an air-water vapor mixture as a function of the water-vapor concentration in the mixture.

Referring now to the figures and first, particularly, to FIG. 1 there is shown therein, as aforementioned, a plot diagram of the velocity of sound $a$ in meters per second of an air-water vapor mixture as a function of the water vapor concentration $x$ of that mixture at different temperatures ($t_1 = 100°$ C $= 373°$ K, $t_2 = 150°$ C $= 423°$ K and $t_3 = 200°$ C $= 473°$ K). As can be readily seen in FIG. 1, the difference of sound velocity in steam compared to that in air is approximately 23%.

Figure 2:
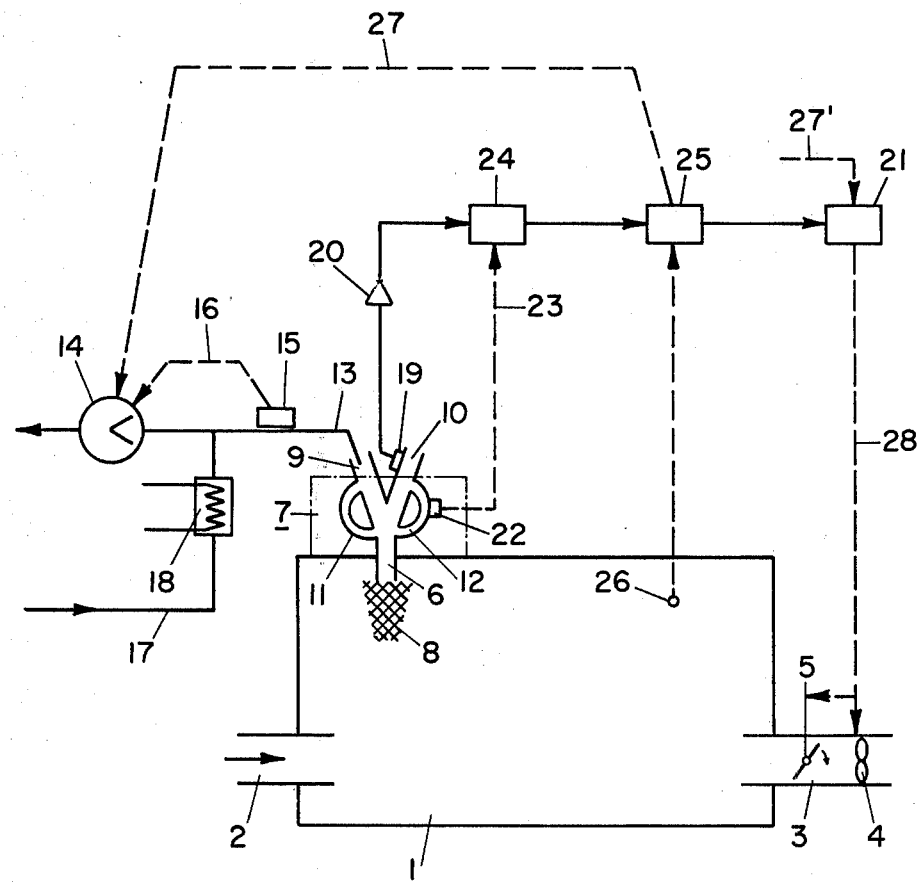
FIG. 2 is a block diagram of the device for determining the mixing ratio of binary gases according to the invention including a fluidic oscillator with associated circuit components.

In the block diagram of FIG. 2, there is shown how the mixing ratio of a gas or the chamber climate in a processing or treatment chamber can be determined and controlled by measuring the velocity of sound by means of a fluidic oscillator.

It is assumed that the gas mixing ratio in a chamber 1 is to be measured or controlled. The chamber 1 is formed with an inlet 2 for a component of the gas mixture, for example, the component that is to be controlled, and an outlet 3 with an exhaust fan or suction ventilator 4 and a throttle 5 or the like. The mixing ratio in the chamber 1 is controllable by an appropriate adjustment of the exhaust fan 4 or the throttle 5 so as to more-or-less strongly exhaust gas from the chamber 1 and correspondingly suck gas into the chamber 1 through the inlet 2.

The inlet 6 of a fluidic oscillator 7 projects into the chamber 1, an air filter 8 being precoupled preferably to the inlet 6. The fluidic oscillator 7 is provided with two feedback lines or coupling conduits 11 and 12 extending from respective outlets 9 and 10 of the fluidic oscillator 7 to the inlet 6 thereof. A suction line 13 of a suction pump 14 is connected to the outlet 9 of the fluidic oscillator 7. Since the fluidic oscillator 7, in accordance with the invention, should be operated within a given pressure range, means 15 for measuring the gas pressure are provided in the suction line 13. In the embodiment of the invention illustrated in FIG. 2, when the pressure exceeds or falls below the permissible pressure range, a signal, which starts up or shuts down a gas pump 14, is transmitted along the operating line 16, from the pressure-measuring instrument 15. In the event danger of gas condensation in the suction-pump 14 should threaten, which could cause irregular operation of the pump, fresh air supply-means 17 are provided upstream or ahead of the inlet to the gas pump 14. It is thereby advantageous, for disturbance-free operation of the suction pump 14, if the fresh air is heated by means of a heat exchanger 18 to the temperature of the gas mixture to be measured.

The signal released by the fluidic oscillator is picked up, for example, by a crystal resonator 19 from the outlet 10 of the oscillator 7 and further transmitted through a preamplifier 20. Before the signal, amplified if necessary, is fed to a control circuit 21, it is corrected, according to the invention, because of possible falsification of the measured value. In the embodiment shown in FIG. 2 the signal is initially corrected for any possible temperature-dependent expansion or elongation of the feedback channels. For this purpose, the temperature of one of the feedback channels, for example the channel 12, is measured with a temperature sensor 22. The thus measured temperature $T_r$ is signalled through a line 12 to an error-correction device 24, at which there is added to the value of the signal arriving from the amplifier 20 the value of the temperature difference $\Delta T = T_r - T_o$ multiplied by a constant factor, $T_r$ being the absolute temperature of the feedback channels 11 and 12, and $T_o$ being predetermined temperature at which the fluidic oscillator 7 has been tuned to a fundamental frequency $f_o$.

The thus corrected signal is then fed to another error-correction device 25 at which the signal is corrected to take into account the actual or absolute temperature $T_g$ of the gas mixture to be measured. The actual temperature of the gas mixture is measured with a temperature sensor 26 in the chamber 1. The error-correction device 25 contains an electronic circuit for multiplying the previously partially corrected signals from the fluidic oscillator with the square root of the quotient of the predetermined temperature $T_o$ and the temperature $T_g$ measured by the temperature sensor 26. For the device according to the invention to be protected from damage or contamination when the gas-mixture temperature to be measured exceeds or falls below predetermined values, the error-correction device 25 transmits a signal through the operating line 27 to the drive of the suction pump 14 for switching off the latter, so that the entire device is rendered inoperative.

After the signal measured with the aid of the fluidic oscillator 7 is corrected in the error correction device 25, the resulting signal is fed to a control circuit or device 21. The control circuit 21, after comparing the signal with a nominal value, 27' transmits the resulting error signal through an operating line 28 to the exhaust fan 4, the throttle 5 or similar adjusting elements, so that the mixing ratio in the chamber 1 is adjusted in the desired direction.

Figure 3:
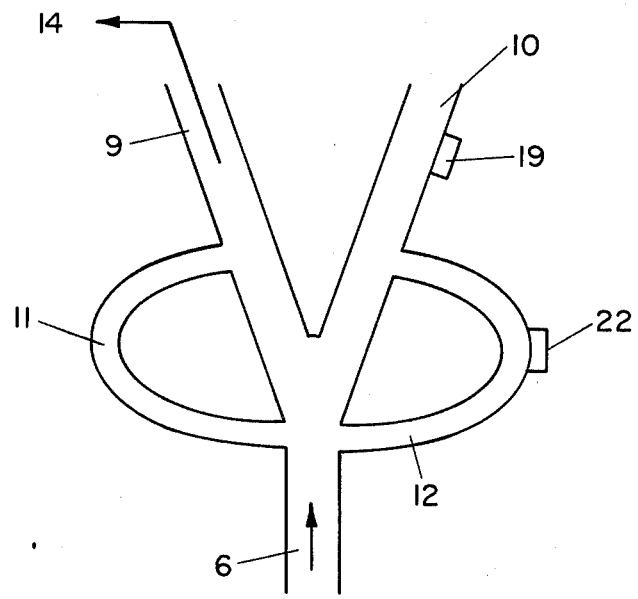
FIG. 3 is an enlarged diagrammatic view of the fluidic oscillator illustrated in FIG. 2, showing the mode of operation thereof.

In FIG. 3, the principal parts of the fluidic oscillator 7 according to FIG. 2, are shown. Similar parts of the oscillator in FIG. 3 are identified by the same reference numerals as in FIG. 2. The oscillator is provided with external feedback lines 11 and 12. The oscillator has been basically developed from a bistable wall-attachment fluid element. Two stable current states exist. One of such wall attachment elements is constructed of a level diffuser 6, which is divided by a wedge downstream from the inlet region into two channels 9 and 10. The basic flow can attach itself stably to one wall or the other as a result of wall stream or flow effects of the diffuser walls, thus flowing out of one of the two outlets 9 and 10. In FIG. 3, both outlets 9 and 10 are shown connected to the inlet 6, so that a feedback oscillator results. If the main flow jumps or skips to one or the other outlet channels 9 or 10, a pressure pulse travels back through one of the feedback conduits 11 or 12, respectively, to the control inlet 6 and switches the main flow over to the other outlet, at which the process is repeated; a natural oscillation is thus excited or initiated.

Thus, as a main gas flow travels from the inlet 6 to the outlet 9, a feedback gas flow is formed in the feedback channel 11 traveling in direction back to the inlet channel 6 and diverts the main gas flow from travel towards the outlet 9 to travel towards the outlet 10. As the main gas flow now travels towards the outlet 10, a feedback gas flow is formed in the feedback channel 12 back to the inlet 6 which, when impinging upon the main gas flow, again diverts the latter back to travel towards the outlet 9.

Obviously, the diverting period is equal to the time required by the gas flow to travel from the diverting location A at the intersection of the outlet channels 9 and 10, into and along the respective outlet channel and return through the respective feedback channel to the diverting location A. Since the wave front of the gas flow expands with the velocity of sound, the aforementioned time period is proportional to the velocity of sound. At constant temperature, however, the velocity of sound is proportional to the density and thereby to the mixing ratio of the gas flowing through the fluidic oscillator.

In accordance with the invention, the one outlet 10 of the fluidic oscillator is closed by the quartz crystal 19. Thus, a gas flow cannot travel through this outlet 10; however, pressure shocks or jolts become perceptible in the channel leading to this outlet 10, which are transmitted through the feedback channel 12 and thereby causes the fluidic oscillator to oscillate. Through the pressure jolts, a charge displacement or shift is produced due to the effect of mechanical pressure in the pressure-sensitive quartz crystal 19 i.e. a so-called piezoelectric crystal, which has two non-illustrated electrodes. This charge displacement or shift produces a voltage or voltage surges (at the frequency of the fluidic oscillator) between both electrodes.

In the invention of the instant application, the velocity of sound per se is not measured but, rather, the frequency of the fluidic oscillator which depends upon or is a function of the velocity of sound. Since the velocity of sound, namely, (at constant pressure) is proportional to the density of a binary gas mixture, the measured frequency must also be proportional to this density. The frequency of the fluidic oscillator naturally depends upon the length of the feedback channels (besides depending upon the temperature and the density). During operation and for one and the same fluidic oscillator, this length is constant, however; then the output signal of the fluidic oscillator is dependent only upon the velocity of sound and the density and the temperature of the gas flowing through the oscillator.

The frequency of oscillation is dependent upon the length of the feedback conduit and the signal propagation velocity. Since pressure pulses are propagated in gases with the velocity of sound and since the velocity of sound is inter alia dependent upon the density of the medium, the oscillating frequency of the oscillator is also a measure of the density of the gas flowing into the oscillator.

Figure 4:
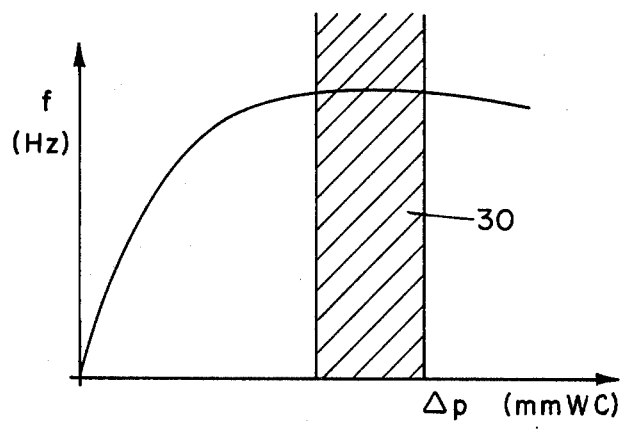
FIG. 4 is a plot diagram showing the oscillating frequency of a fluidic oscillator as a function of the applied differential pressure.

The oscillating frequency of the fluidic oscillator according to the invention is plotted in FIG. 4 as a function of the applied differential pressure $\Delta p$. Although the oscillating frequency $f$ increases at first with increasing differential pressure, there are regions in the characteristic curve shown where the oscillating frequency $f$ is practically independent of any changes in the differential pressure. It is indeed in this region 30, shown shaded in FIG. 4, where the fluidic oscillator is supposed to operate in accordance with the invention. Thereby, when any small changes of pressure occur at the oscillator, they do not have any significant effect on the oscillating frequency to be measured.

Figure 5:
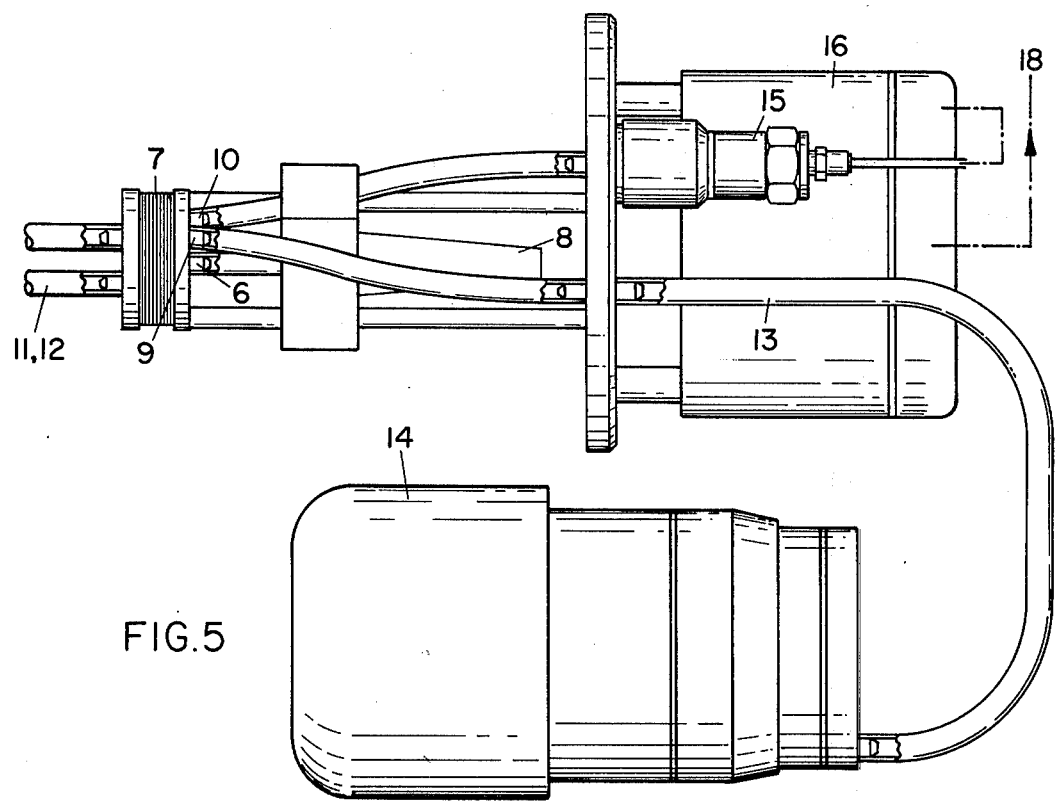
FIG. 5 is an elevational view of an actual fluidic oscillator.

In FIG. 5, details of the construction of an actual fluidic oscillator are shown, corresponding parts thereof and of FIGS. 2 and 3 being identified by the same reference numerals.

Figure 6:
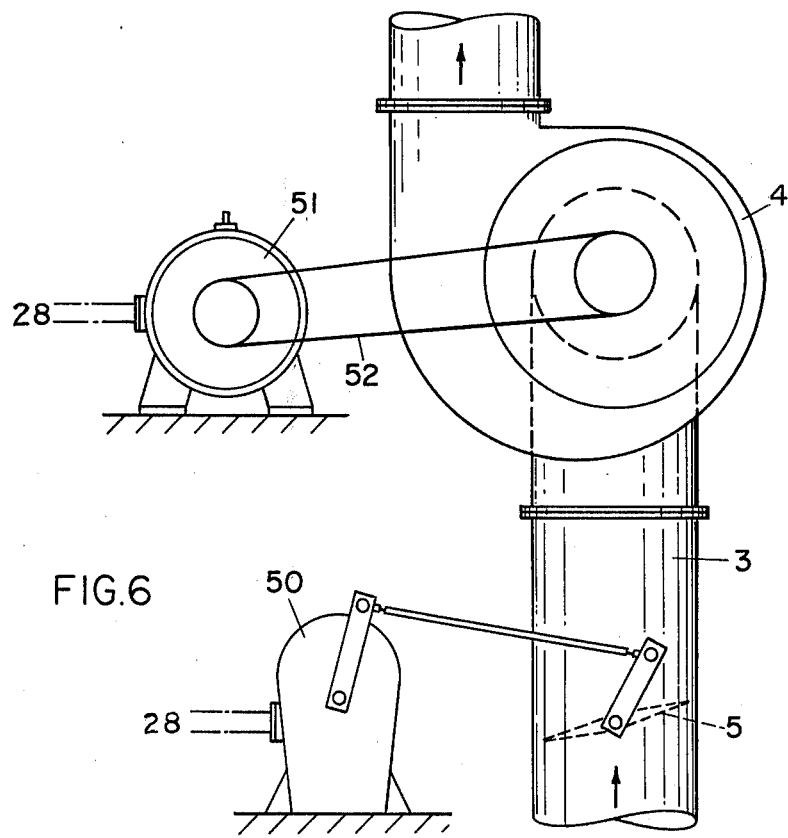
FIG. 6 is a diagrammatic elevational view of an exhaust fan and of a throttle of a fluidic oscillator according to the invention.

In FIG. 6, details of the construction of the exhaust fan 4 and the throttle valve 5 of FIG. 2 are shown. A drive motor 51 which is connected to an electric voltage or current supply by leads 28 coming from the control unit 21 (FIG. 2) drives the exhaust fan 4 by means of a belt 52 when responsive to the control unit 21.

The throttle 5 disposed in the conduit 3 is positioned by means of a servo-motor 50 which may be connected to the electric supply through the same leads 28 extending from the control unit 21. The flow of gas from the chamber 1 (not shown in FIG. 6) passes through the conduit 3 in accordance with the suction pressure provided by the fan 4 and/or in accordance with the flow cross section in the conduit 3 adjusted by the throttle 5, controlled by the control system 21 of FIG. 2.

Figure 7:
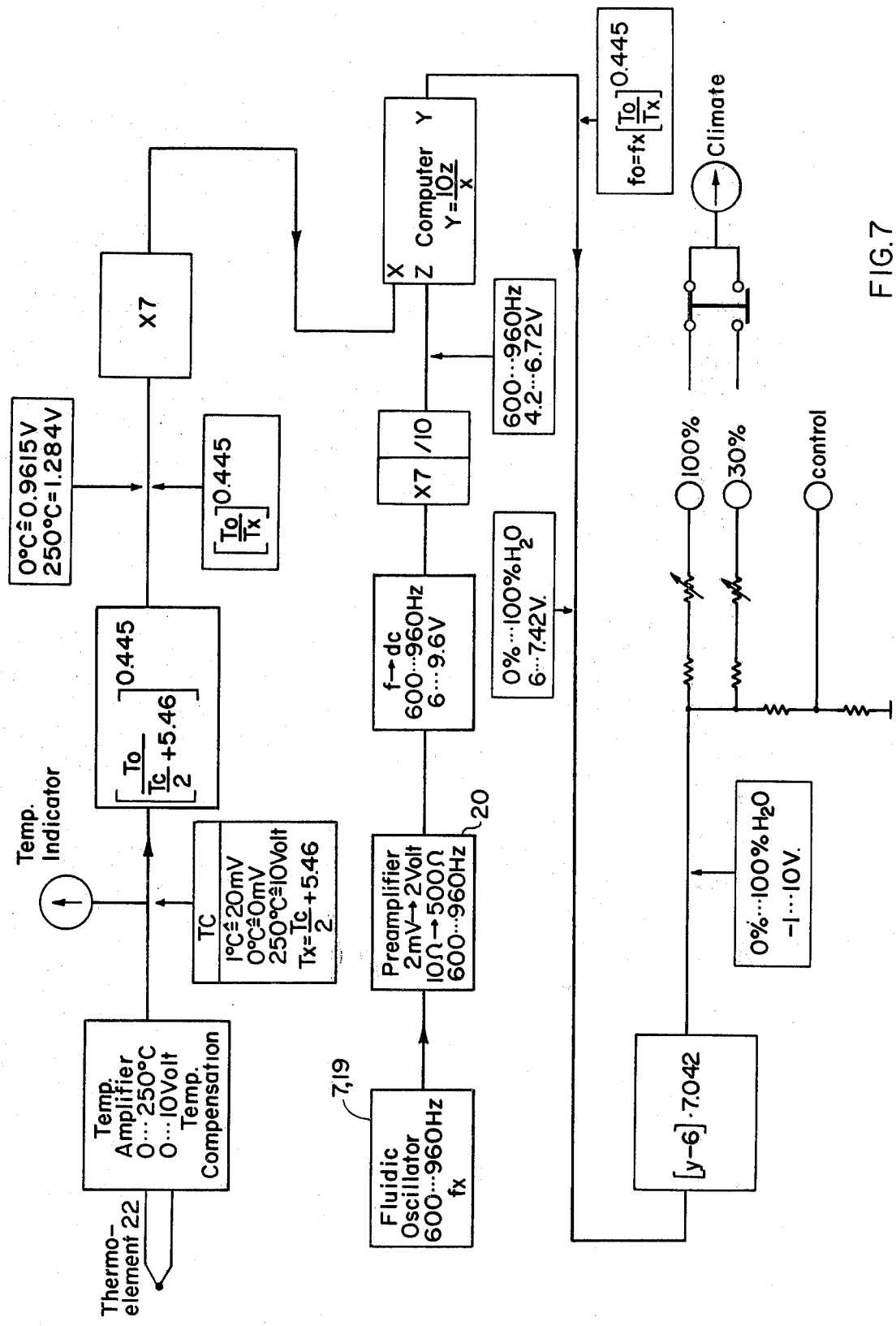
FIG. 7 is a block circuit diagram of an embodiment of the invention showing details for effecting temperature compensation of the fluidic oscillator frequency according to the invention.
Figure 8:
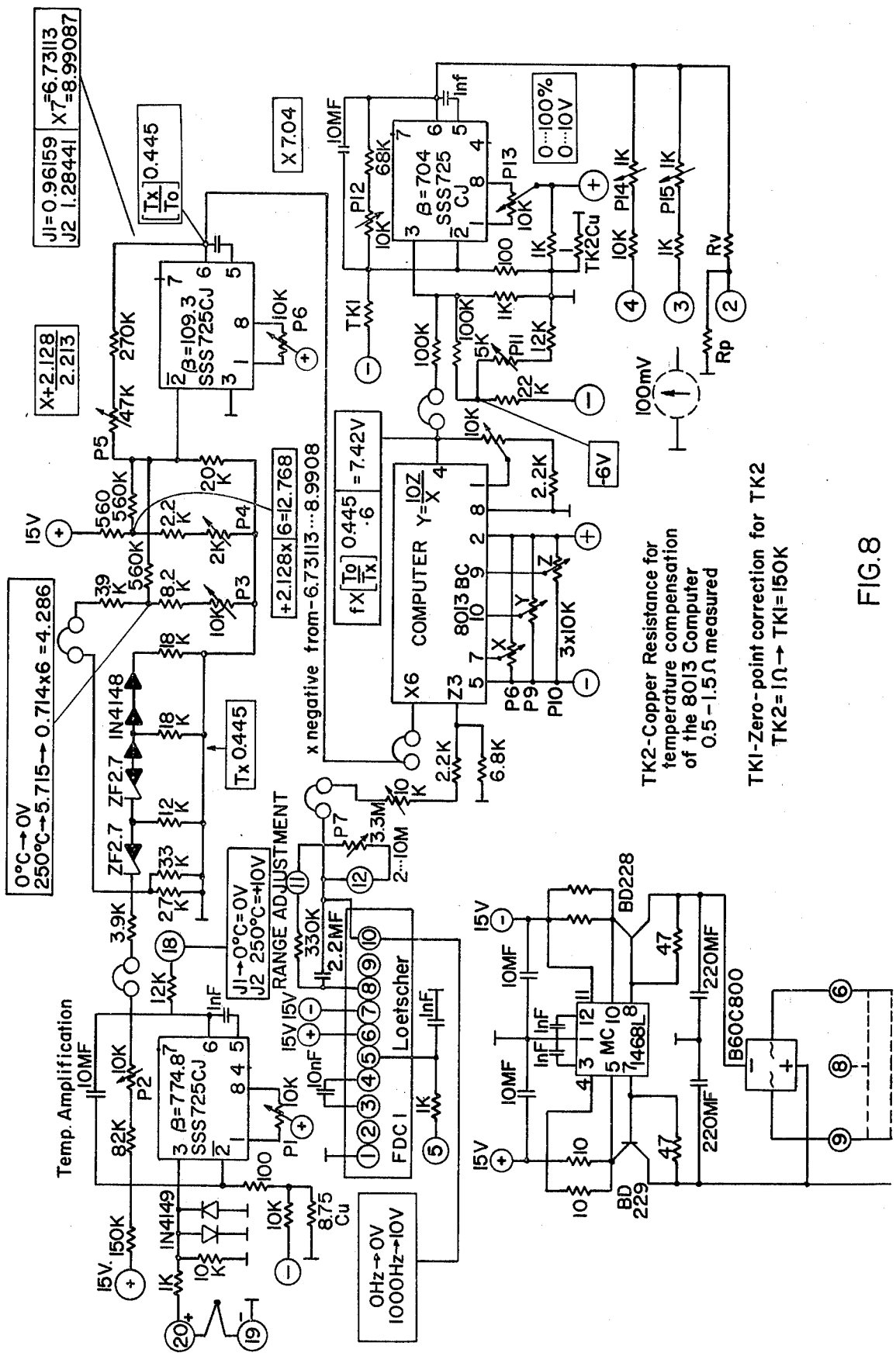
FIG. 8 is a circuit diagram of an electronic system K1 corresponding to the block diagram of FIG. 7.

The block diagram of FIG. 7 provides a more detailed illustration of one embodiment of the invention for providing temperature compensation of the frequency of the fluidic oscillator, and FIG. 8 is a diagram of an electronic circuit (K1) illustrating the components and their connections, as well as other pertinent information corresponding to the block diagram of FIG. 7. In FIG. 8, the various symbols and abbreviations correspond to engineering standards adopted in Germany.

As can be seen in FIG. 7, the temperature at the thermocouple or thermoelement 22 is measured and subsequently amplified in terms of ° C. A typical temperature monitoring circuit for such a purpose may be found on page 763, Sourcebook of Electronic Circuits, published 1968, by McGraw-Hill. These temperatures are to be used in equations wherein absolute temperature ° K is required. The temperature-measuring device of the embodiment of FIG. 7 operates within a range of 0° to 250° C. Corresponding nonlinear formulas which hold for the temperature measurement are therefore especially designed for this range of temperatures. Several constants have been introduced into these formulas in order to be able to insert temperature values measured in ° C directly into the formulas. A typical adder circuit for use in error correction device 24 can be found on page 123 of the above-mentioned Sourcebook of Electronic Circuits.

Since the computer actually employed in the embodiment of FIG. 7 provided adequate accuracy only when the introduced voltage values attained given minimum values such as 5 to 10 volts, for example, the voltages derived from the temperature measurement were multiplied by 7 (note the box labeled XT) and only then introduced into the computer. An example of a typical multiplier circuit for use in error correction device 25 may be found on page 415 of the above Sourcebook of Electronic Circuits.

On the other hand, the frequency values from the fluidic oscillator were transmitted through a preamplifier to a frequency-direct-voltage converter and thereby converted into a frequency-proportional direct-voltage signal. An example of such a circuit is found on page 146, Sourcebook of Electronic Circuits. Thereafter, the direct voltage signal to which the fluidic oscillator frequency value had been converted (just as in the case of the aforementioned signal coming from the thermoelement 22), is multiplied by 7. The resulting value, in the case of this embodiment of FIG. 7, was divided by 10 because the computer employed in the embodiment automatically multiplied by 10.

In order to match the output signal of the computer to the scale of the measuring device adjusted in percentages of water vapor, the output value $y$ of the computer, in this special case, is diminished by 6, and the remainder is then multiplied by 7.042.

In FIG. 9, there is shown a wiring diagram for the electronic system K1 of FIG. 8. At the right-hand side of FIG. 9, the various connections to the inputs of the K1 electronic system are shown and are suitably labeled so as to require no further explanation. Similarly, the outputs shown at the bottom of FIG. 9 are suitably labeled so as to require no further detailed description.

In FIG. 10, the preamplifier 20 of the fluidic oscillator is shown. The symbols employed in the circuit diagram of FIG. 10 are those common in practice in Germany, and the various components have been suitably labeled to show the values thereof in this embodiment of the preamplifier 20.

It is claimed:

1. Device for determining the mixing ratio of binary gases in a mixture thereof by measuring the velocity of sound in the gas mixture, that velocity being determined by the oscillating frequency of a fluidic oscillator comprising a fluidic oscillator tuned to a fundamental frequency ($f_o$) at a predetermined temperature ($T_0$) in air, said fluidic oscillator having inlet and outlet means and feedback means connecting said outlet means to said inlet means, means for detecting the oscillating frequency of said fluidic oscillator, which determines the velocity of sound in the gas mixture, and transmitting a signal corresponding thereto, measuring means for measuring absolute gas temperature ($T_g$) of the gas mixture at a location other than in said feedback means, correction means operatively connected to said means for measuring said absolute gas temperature ($T_g$) for correcting, by a correction factor proportional to the square root of said absolute gas temperature ($T_g$), the value of the velocity of sound in the gas mixture determined by the oscillating frequency of said fluidic oscillator and represented by said transmitted signal, measuring means for measuring absolute temperature ($T_r$) of the gas mixture in said feedback means, correction means operatively connected to said means for measuring said feedback absolute temperature ($T_r$) for correcting, by a correction factor proportional to the difference between said feedback absolute temperature ($T_r$) and said predetermined temperature ($T_o$), the value of the velocity of sound in the gas mixture determined by the oscillating frequency of said fluidic oscillator and represented by said transmitted signal, and pump means for pumping the gas mixture through said fluidic oscillator, said pump means being adjusted to a range of pressures wherein oscillating frequencies produced in said fluidic oscillator and serving to determine the respective velocity of sound in the gas mixture being pumped therethrough are independent of variations in the gas pressure.

2. Device according to claim 1 wherein said first-mentioned correction means include means for multiplying the value of the velocity of sound in the gas mixture determined by the oscillating frequency of said fluidic oscillator and represented by said transmitted signal, by the square root of the quotient of said predetermined temperature ($T_o$) and said absolute gas temperature ($T_g$).

3. Device according to claim 1 wherein said last-mentioned correction means include means for adding said difference between said feedback absolute temperature ($T_r$) and said predetermined ($T_o$), multiplied by a constant factor, to the value of the velocity of sound in the gas mixture determined by the detected oscillating frequency of said fluidic oscillator and represented by said transmitted signal.

4. Device according to claim 1 including means for shutting down said fluidic oscillator whenever the temperature of the gas mixture exceeds and falls below a predetermined range of temperatures.

5. Device according to claim 1 including means for measuring the pressure of the gas mixture in said fluidic oscillator and for shutting down said fluidic oscillator whenever the pressure of the gas mixture therein exceeds and falls below a predetermined range of pressures.

6. Device according to claim 1 wherein said pump means is a suction pump.

7. Device according to claim 1 including means interposed between said fluidic oscillator and said pump means for adding air to said gas mixture.

8. Device according to claim 7 including means for heating the air to the temperature of said gas mixture before adding the air thereto.

9. Device according to claim 1 including means for controlling the gas mixture in accordance with the signal from said first and last mentioned correction means with respect to a reference signal.

* * * * *